United States Patent
Hagiwara

(10) Patent No.: US 9,378,567 B2
(45) Date of Patent: Jun. 28, 2016

(54) IMAGE GENERATING METHOD, IMAGE GENERATING APPARATUS AND RADIATION TOMOGRAPHIC IMAGING APPARATUS, AND PROGRAM THEREFOR

(71) Applicant: GE MEDICAL SYSTEMS GLOBAL TECHNOLOGY COMPANY, LLC, Waukesha, WI (US)

(72) Inventor: Akira Hagiwara, Tokyo (JP)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 337 days.

(21) Appl. No.: 13/788,682

(22) Filed: Mar. 7, 2013

(65) Prior Publication Data

US 2013/0243152 A1 Sep. 19, 2013
US 2014/0146938 A9 May 29, 2014

(30) Foreign Application Priority Data

Mar. 14, 2012 (JP) .................................. 2012-57071

(51) Int. Cl.
*G06T 11/00* (2006.01)
*A61B 6/03* (2006.01)

(52) U.S. Cl.
CPC ............... *G06T 11/005* (2013.01); *A61B 6/032* (2013.01)

(58) Field of Classification Search
CPC ........ A61B 6/03; A61B 6/032; A61B 6/4078; G06T 11/00; G06T 11/003; G06T 11/005; G06T 11/006
See application file for complete search history.

(56) References Cited

U.S. PATENT DOCUMENTS

| 3,983,398 A | 9/1976 | Boyd |
| RE30,947 E * | 5/1982 | Boyd ............................. 378/14 |
| 4,979,111 A | 12/1990 | Nishimura |
| 5,047,931 A | 9/1991 | Lin |

(Continued)

FOREIGN PATENT DOCUMENTS

| JP | 2011188030 | 7/1999 |
| JP | 2012-005757 | 1/2012 |

OTHER PUBLICATIONS

Nalcioglu, et al. "Limited Field of View Reconstruction in Computerized Tomography", IEEE Transactions on Nuclear Science, vol. NS-26, No. 1, Feb. 1979.*
Basu, Samit, et al., "A Compact CT Geometry: Theory and Practice," The First International Conference on Image Formation in X-Ray Computed Tomography, Jun. 2010, pp. 73-75.

(Continued)

*Primary Examiner* — Thomas R Artman
(74) *Attorney, Agent, or Firm* — Lucas Divine

(57) ABSTRACT

An image generating method is provided. The method includes performing a rearrangement process and an interpolation process on fan beam projection data, the fan beam projection data acquired by a scan that includes rotating a radiation source and a detector having a plurality of detecting elements arranged in a channel direction, wherein the interpolation process generates equally-spaced parallel beam projection data in which channel-direction intervals are equal therebetween, and wherein the interpolation process is performed with respect to a plurality of view directions. The method further includes performing a back-projection process on the equally-spaced parallel beam projection data to thereby reconstruct an image, wherein the channel-direction intervals between the equally-spaced parallel beam projection data are smaller than a reference interval obtained by dividing an interval between the detecting elements in the channel direction by a projection enlargement rate.

5 Claims, 12 Drawing Sheets

(56) References Cited

U.S. PATENT DOCUMENTS

| | | | |
|---|---|---|---|
| 5,216,601 A | 6/1993 | Crawford et al. | |
| 5,406,479 A | 4/1995 | Harman | |
| 6,169,779 B1 | 1/2001 | Lai | |
| 6,359,956 B1 | 3/2002 | Hsieh et al. | |
| 6,411,670 B1 | 6/2002 | Besson | |
| 6,415,012 B1* | 7/2002 | Taguchi et al. | 378/15 |
| 8,116,426 B2 | 2/2012 | Hein et al. | |
| 2008/0095304 A1 | 4/2008 | Grass et al. | |
| 2013/0243152 A1* | 9/2013 | Hagiwara | 378/19 |
| 2013/0343508 A1* | 12/2013 | Hagiwara | 378/4 |
| 2014/0146938 A9* | 5/2014 | Hagiwara | 378/19 |

OTHER PUBLICATIONS

Buzug, Thorsten M., "Rebinning of the Fan-Beams," Computed Tomography, 2008, pp. 265-270.

EP Search Report and Written Opinion dated Feb. 17, 2014, issued in connection with corresponding EP Application No. 13157859.3.

Unofficial translation of CN Office Action, issued Jan. 4, 2016, in relation to corresponding CN Application 201310081392.4.

O. Nalcioglu et al; "Limited field of view reconstruction in computerized tomography", "IEEE Transactions on Nuclear Science", vol. 26, Issue 1, Feb. 1979, pp. 546-551, University of California-Irvine, Irvine, CA.

* cited by examiner

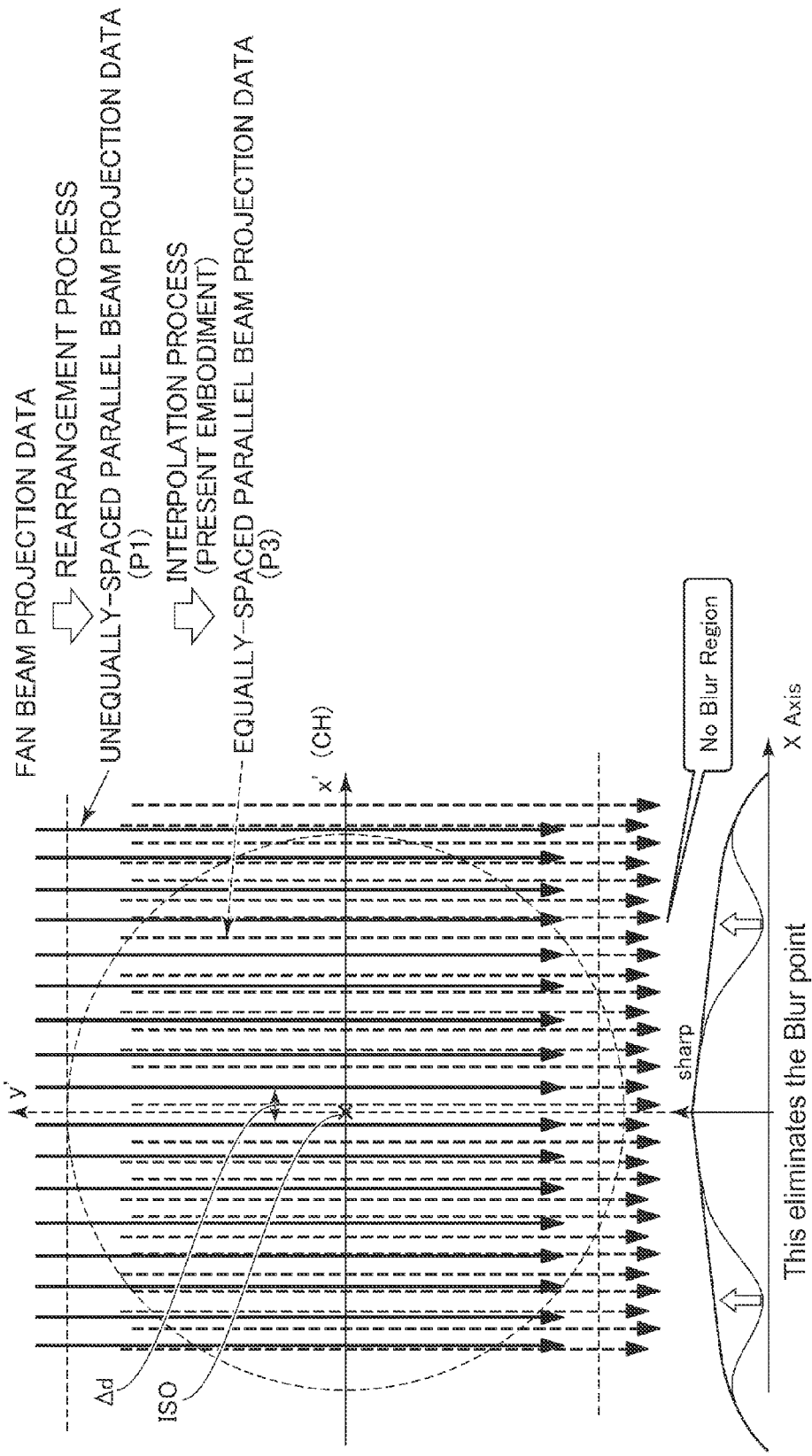

IMAGE GENERATING METHOD, IMAGE GENERATING APPARATUS AND RADIATION TOMOGRAPHIC IMAGING APPARATUS, AND PROGRAM THEREFOR

CROSS REFERENCE TO RELATED APPLICATIONS

This application claims the benefit of Japanese Patent Application No. 2012-57071 filed Mar. 14, 2012, which is hereby incorporated by reference in its entirety.

BACKGROUND OF THE INVENTION

The present invention relates to an image generating method, an image generating apparatus and a radiation tomographic imaging apparatus which fan-para convert radiation projection data and perform back projection thereon to thereby reconstruct an image, and a program therefor.

In a third-generation X-ray CT (Computed Tomography) apparatus, X rays of a fan beam are used in the acquisition of projection data. There is a case in which the so-acquired fan beam projection data are converted to parallel beam projection data, followed by being subjected to a back-projection process to reconstruct an image.

This conversion is generally referred to as "fan-para conversion". An image reconstructing method using the fan-para conversion is called "fan-para conversion method". The fan-para conversion method is principally performed with the aim of ensuring the uniformity of CT values, suppressing artifacts at the time that MPR (Multi-Plane Reconstruction) is carried out, reducing a computational processing amount, and so on.

On the other hand, when fan beam projection data of plural views are taken apart every data in a channel direction and rearranged in a simplistic form to acquire parallel beam projection data, the positions of radiation paths corresponding to the respective data are unequally spaced in the channel direction.

Since, however, Fourier transform corresponding to frequency conversion is performed on the parallel beam projection data after the fan-para conversion in the fan-para conversion method, the radiation paths corresponding to the respective data need to be arranged at equal intervals in the channel direction.

Thus, normally, when the fan-para conversion is performed, not only a rearrangement process but also an interpolation process in the channel direction is performed on the fan beam projection data to acquire equally-spaced parallel beam projection data in which the positions of radiation paths are arranged at equal integrals in the channel direction (refer to, for example, paragraph [0004] of Japanese Unexamined Patent Publication No. 2012-005757).

When, however, the equally-spaced parallel beam projection data acquired by performing the interpolation process in the channel direction are compared with pre-interpolation process data (i.e., data before the interpolation processing), more errors from true values are included therein, thereby leading to a reduction in the spatial resolution of a reconstructed image.

With the foregoing in view, there has been a demand for a technology that enables a reduction in the spatial resolution of the reconstructed image to be suppressed even if the fan-para conversion is performed.

BRIEF DESCRIPTION OF THE INVENTION

In a first aspect, an image generating method is provided. The image generating method includes a data conversion step for performing a rearrangement process and an interpolation process on fan beam projection data of a plurality of views acquired by a scan for rotating a radiation source and a detector having a plurality of detecting elements arranged in a channel direction about a target to thereby acquire equally-spaced parallel beam projection data in which channel-direction intervals are equal, with respect to a plurality of view directions, and an image reconstruction step for performing a back-projection process on the acquired equally-spaced parallel beam projection data to thereby reconstruct an image, in which the interval between the equally-spaced parallel beam projection data in the channel direction is smaller than a reference interval obtained by dividing the interval of arrangement of the detecting elements in the channel direction by a projection enlargement rate at a detection surface of the detector at the time when the center of rotation of each of the radiation source and the detector is taken as a reference.

In a second aspect, the image generating method according to the first aspect is provided, in which the interval between the equally-spaced parallel beam projection data in the channel direction is 1/N (where N is an integer greater than or equal to 2) of the reference interval.

In a third aspect, the image generating method according to the second aspect is provided, in which N is any of the integers ranging from 2 to 4.

In a fourth, aspect the image generating method according to the second or third aspect is provided, in which the position of each of the equally-spaced parallel beam projection data in the channel direction is set to substantially overlap with the position in the channel direction, of each of unequally-spaced parallel beam projection data obtained by performing a rearrangement process on the fan beam projection data, in the neighborhood of the center of rotation.

In a fifth aspect, the image generating method according to any one of the first through fourth aspects is provided, in which in the data conversion step, the order of the interpolation process is changed according to the distance of data attempted to be acquired by the interpolation process from the center of rotation.

In a sixth aspect, the image generating method according to any one of the first through fourth aspects is provided, in which in the data conversion step, weighting to the original data used in the interpolation process is changed according to the distance between the position of the data attempted to be acquired by the interpolation process and the position of the original data used in the interpolation process.

In a seventh aspect, an image generating apparatus is provided. The image generating apparatus includes a data converting unit for performing a rearrangement process and an interpolation process on fan beam projection data of a plurality of views acquired by a scan for rotating a radiation source and a detector having a plurality of detecting elements arranged in a channel direction about a target to thereby acquire equally-spaced parallel beam projection data in which channel-direction intervals are equal, with respect to a plurality of view directions, and an image reconstructing unit for performing a back-projection process on the acquired equally-spaced parallel beam projection data to thereby reconstruct an image, in which the interval between the equally-spaced parallel beam projection data in the channel direction is smaller than a reference interval obtained by dividing the interval of arrangement of the detecting elements in the channel direction by a projection enlargement rate at a detection surface of the detector at the time that the center of rotation of each of the radiation source and the detector is taken as a reference.

In an eighth aspect, the image generating apparatus according to the seventh aspect is provided, in which the interval between the equally-spaced parallel beam projection data in the channel direction is 1/N (where N is an integer greater than or equal to 2) of the reference interval.

In a ninth aspect, the image generating apparatus according to the eighth aspect is provided, in which N is any of the integers ranging from 2 to 4.

In a tenth aspect, the image generating apparatus according to the eighth or ninth aspect is provided, in which the position of each of the equally-spaced parallel beam projection data in the channel direction is set to substantially overlap with the position in the channel direction, of each of unequally-spaced parallel beam projection data obtained by performing a rearrangement process on the fan beam projection data, in the neighborhood of the center of rotation.

In an eleventh aspect, the image generating apparatus according to any one of the seventh through tenth aspects is provided, in which the data converting unit changes the order of the interpolation process according to the distance of data attempted to be acquired by the interpolation process from the center of rotation.

In a twelfth aspect, the image generating apparatus according to any one of the seventh through tenth aspects is provided, in which the data converting unit changes weighting to the original data used in the interpolation process according to the distance between the position of the data attempted to be acquired by the interpolation process and the position of the original data used in the interpolation process.

In a thirteenth aspect, a radiation tomographic imaging apparatus is provided. The radiation tomographic imaging apparatus includes a radiation source, a detector having a plurality of detecting elements arranged in a channel direction, a data acquiring unit for acquiring fan beam projection data of a plurality of views by a scan for rotating the radiation source and the detector about a target, a data converting unit for performing a rearrangement process and an interpolation process on the acquired fan beam projection data to thereby acquire equally-spaced parallel beam projection data in which channel-direction intervals are equal, with respect to a plurality of view directions, and an image reconstructing unit for performing a back-projection process on the acquired equally-spaced parallel beam projection data to thereby reconstruct an image, in which the interval between the equally-spaced parallel beam projection data in the channel direction is smaller than a reference interval obtained by dividing the interval of arrangement of the detecting elements in the channel direction by a projection enlargement rate at a detection surface of the detector at the time that the center of rotation of each of the radiation source and the detector is taken as a reference.

In a fourteenth aspect, the radiation tomographic imaging apparatus according to the thirteenth aspect is provided, in which the interval between the equally-spaced parallel beam projection data in the channel direction is 1/N (where N is an integer greater than or equal to 2) of the reference interval.

In a fifteenth aspect, the radiation tomographic imaging apparatus according to the fourteenth aspect is provided, in which N is any of the integers ranging from 2 to 4.

In a sixteenth aspect, the radiation tomographic imaging apparatus according to the fourteenth or fifteenth aspect is provided, in which the position of each of the equally-spaced parallel beam projection data in the channel direction is set to substantially overlap with the position of each of unequally-spaced parallel beam projection data obtained by performing a rearrangement process on the fan beam projection data, in the neighborhood of the center of rotation.

In a seventeenth aspect, the radiation tomographic imaging apparatus according to any one of the thirteenth through sixteenth aspects is provided, in which the data converting unit changes the order of the interpolation process according to the distance of data attempted to be acquired by the interpolation process from the center of rotation.

In an eighteenth aspect, the radiation tomographic imaging apparatus according to any one of the thirteenth through sixteenth aspects is provided, in which the data converting unit changes weighting to the original data used in the interpolation process according to the distance between the position of the data attempted to be acquired by the interpolation process and the position of the original data used in the interpolation process.

In a nineteenth aspect, the radiation tomographic imaging apparatus according to any one of the thirteenth through eighteenth aspects is provided, in which the data acquiring unit assigns views for performing the acquisition of actual data to a rotating angle per rotation of each of the radiation source and the detector 1200 more to thereby acquire the fan beam projection data of the plural views.

In a twentieth aspect, a program is provided. The program allows a computer to function as data converting unit for performing a rearrangement process and an interpolation process on fan beam projection data of a plurality of views acquired by a scan for rotating a radiation source and a detector having a plurality of detecting elements arranged in a channel direction about a target to thereby acquire equally-spaced parallel beam projection data in which channel-direction intervals are equal, with respect to a plurality of view directions, and image reconstructing unit for performing a back-projection process on the acquired equally-spaced parallel beam projection data to thereby reconstruct an image, in which the interval between each radiation path in the channel direction is smaller than a reference interval obtained by dividing the interval of arrangement of the detecting elements in the channel direction by a projection enlargement rate at a detection surface of the detector at the time that the center of rotation of each of the radiation source and the detector is taken as a reference.

According to the above aspects, equally-spaced parallel beam projection data are acquired in such a manner that when fan-para conversion is performed, the interval between each data in a channel direction becomes an interval smaller than a reference interval obtained by dividing the interval of arrangement of detecting elements in the channel direction by a projection enlargement rate at a detection surface of a detector at the time that a so-called iso-center is set as a reference. Therefore, pre-interpolation data high in accuracy or post-interpolation data (i.e., data after interpolation processing) close thereto can be more used in a back-projection process. Even if the fan-para conversion is performed, a reduction in the spatial resolution of a reconstructed image can be suppressed.

BRIEF DESCRIPTION OF THE DRAWINGS

FIG. 7 is a diagram for describing an interpolation process on parallel beam projection data in a channel direction by an exemplary method.

DETAILED DESCRIPTION OF THE INVENTION

An exemplary embodiment will hereinafter be described. Incidentally, the disclosure is not limited by or to the exemplary embodiment.

First Embodiment

Figure 1:
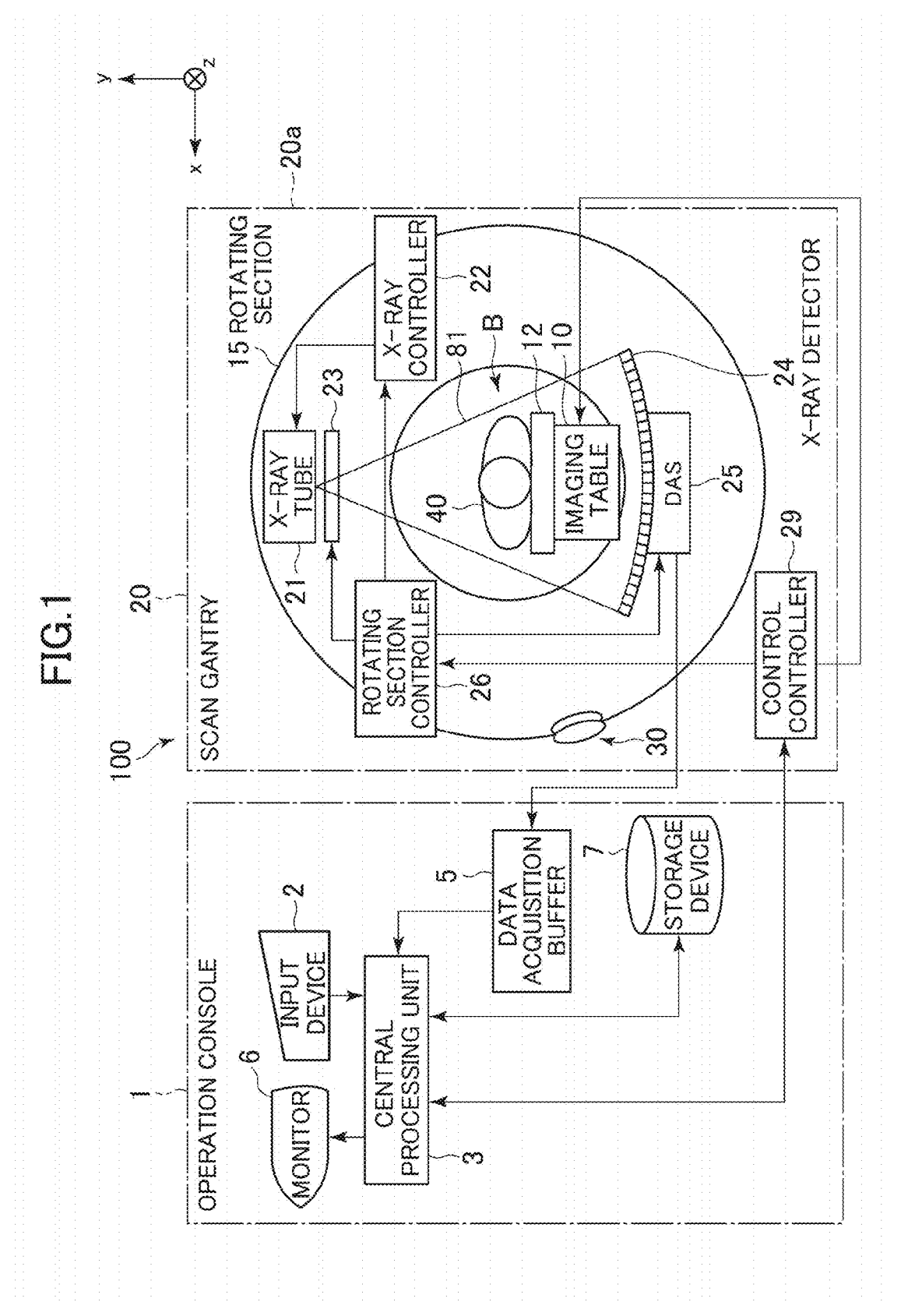
FIG. 1 is a diagram schematically showing a configuration of an exemplary X-ray CT apparatus.

FIG. 1 is a diagram schematically showing a configuration of an X-ray CT apparatus according to the exemplary embodiment.

The X-ray CT apparatus 100 is equipped with an operation console 1, a imaging table 10 and a scan gantry 20.

The operation console 1 is equipped with an input device 2 which accepts an input from an operator, a central processing unit 3 which executes control of respective parts for performing subject's imaging, data processing for generating an image, etc., a data acquisition buffer 5 which acquires or collects data acquired by the scan gantry 20, a monitor 6 which displays each image thereon, and a storage device 7 which stores programs, data, etc. therein.

The imaging table 10 is equipped with a cradle 12 which conveys a subject 40 to a cavity portion B of the scan gantry 20 with the subject 40 placed thereon. The cradle 12 is elevated and linearly moved horizontally by a motor built in the imaging table 10. Incidentally, in the exemplary embodiment, the direction of a body axis of the subject 40, i.e., the horizontal linear moving direction of the cradle 12 is assumed to be a z direction, its vertical direction is assumed to be a y direction, and its horizontal direction orthogonal to the z and y directions is assumed to be an x direction.

The scan gantry 20 has a rotating section 15 and a body section 20a which rotatably supports the rotating section 15. The rotating section 15 is provided with an X-ray tube 21, an X-ray controller 22 which controls the X-ray tube 21, an aperture 23 which shapes X-rays 81 generated from the X-ray tube 21 into a fan beam or a cone beam, an X-ray detector 24 which detects the X-rays 81 penetrated through the subject 40, and a rotating section controller 26 which controls the X-ray controller 22 and the aperture 23. The body section 20a is equipped with a control controller 29 which performs communication of control signals or the like with the operation console 1 and the imaging table 10. The rotating section 15 and the body section 20a are electrically coupled to each other via a slip ring 30.

The X-ray tube 21 and the X-ray detector 24 are disposed opposite to each other with an imaging space in which the subject 40 is placed, i.e., the cavity portion B of the scan gantry 20 interposed therebetween. When the rotating section 15 is rotated, the X-ray tube 21 and the X-ray detector 24 are rotated about the subject 40 while their positional relation is being maintained. The X-rays 81 shown in the form of the fan beam or cone beam, which are radiated from the X-ray tube 21 and shaped by the aperture 23, penetrate the subject 40 and are applied onto a detection surface of the X-ray detector 24.

Incidentally, here, the direction of expansion of the X-rays 18 shown in the form of this fan beam or cone beam at an xy plane is assumed to be shown as a channel direction (CH direction), the direction of expansion thereof in the z direction or the z direction itself is assumed to be shown as a slice direction (SL direction), and the direction thereof to the center of rotation of the rotating section 15 at the xy plane is assumed to be shown as an iso-center direction (I direction).

The X-ray detector 24 includes a plurality of detecting elements 24i arranged in the channel and slice directions. Incidentally, the number of the detecting elements in the channel direction is, for example, about 900 within an angular range of 60°. The interval of arrangement of the detecting element is, for example, about 1 mm.

Figure 2:
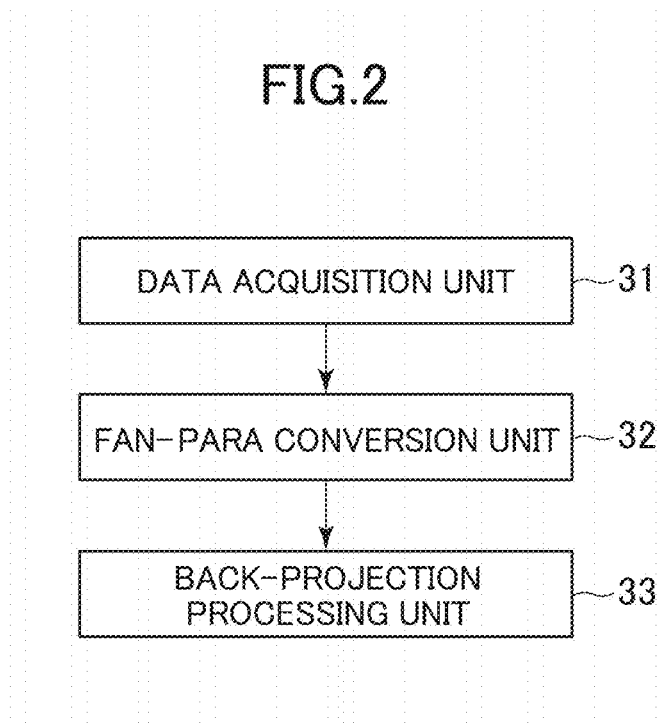
FIG. 2 is a functional block diagram illustrating a configuration of a section related to an image generating process in the X-ray CT apparatus.

FIG. 2 is a functional block diagram showing a configuration of a section related to an image generating process in the X-ray CT apparatus. As shown in FIG. 2, the X-ray CT apparatus 100 is equipped with a data acquisition unit 31, a fan-para conversion unit 32 and a back-projection processing unit 33. The data acquisition unit 31 runs a scan to acquire fan beam projection data of plural views. The fan-para conversion unit 32 performs a fan-para conversion process on the acquired fan beam projection data to acquire equidistant or equally-spaced parallel beam projection data. The back-projection processing unit 33 performs a back-projection process on the thus-acquired equally-spaced parallel beam projection data to reconstruct an image.

The functions of these units will be explained below in more detail.

Figure 3:
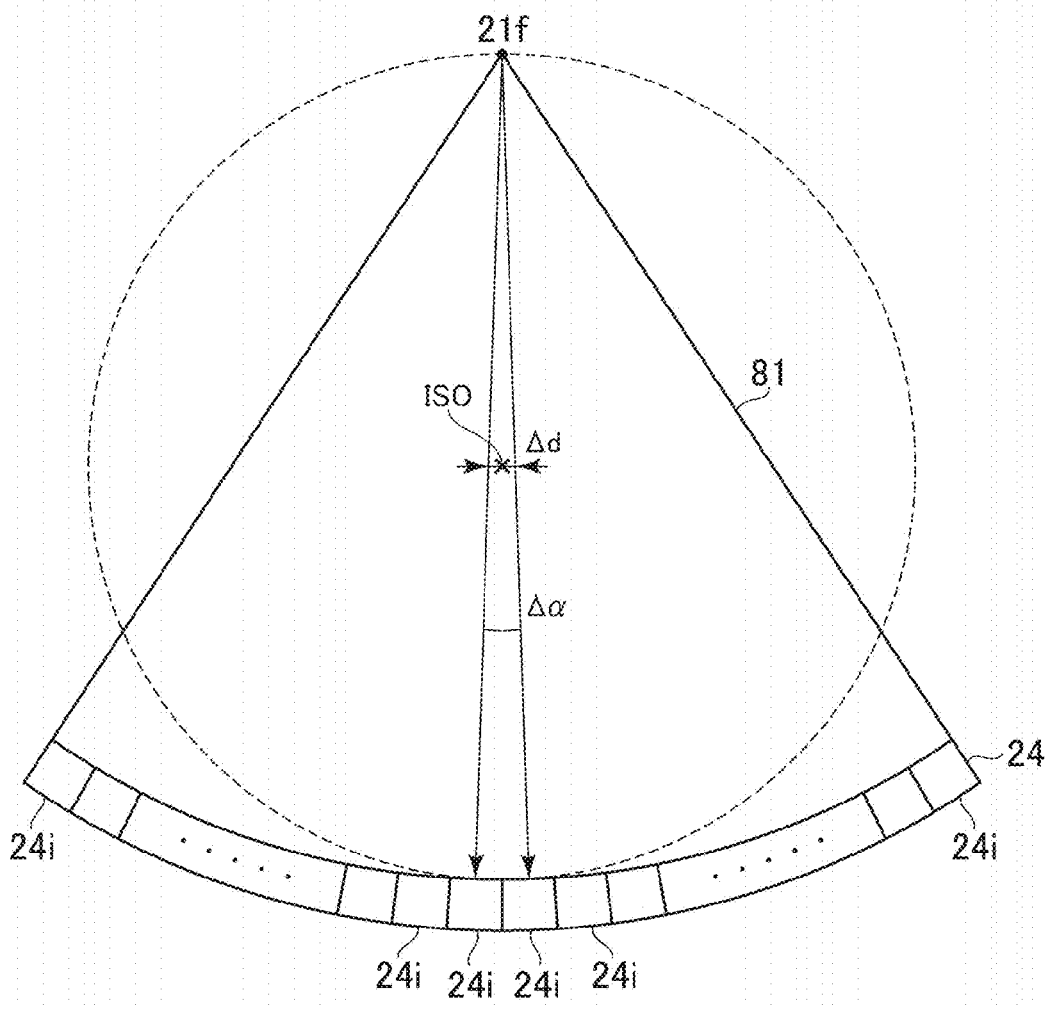
FIG. 3 is a diagram depicting a geometry at data acquisition.

FIG. 3 is a diagram showing a geometry at data acquisition.

The data acquisition unit 31 controls the scan gantry 20 to run a scan, thereby acquiring fan beam projection data of plural views. The fan beam projection data are of projection data in which X-ray paths corresponding to respective data are expanded in fan-beam form, i.e., radially in a predetermined angular range.

In the exemplary embodiment, as shown in FIG. 3, the above scan is performed while evenly allocating a predetermined number of views to a turning or rotating angle corresponding to one rotation in such a manner that a rotating angle corresponding to one view becomes substantially equal to a rotating angle $\Delta\alpha$ corresponding to the interval of arrangement of the detecting elements in the channel direction.

Incidentally, the fan beam projection data of the respective views may all be actual data based directly on detected signals of the detecting elements 24i and not subjected to an interpolation process or the like. Some of the fan beam projection data may be acquired by interpolation of actual data in a view direction. When the assignment of views at which actual data are acquired, is however made excessively rough depending greatly on the interpolation in the view direction, it exerts a bad influence on the spatial resolution of a reconstructed image. Therefore, the number of views which are assigned to the turning angle corresponding to one rotation and at which the acquisition of actual data is performed, is set to, for example, at least 800 views, 1200 views or more, or 1600 views or more.

Figure 4B:
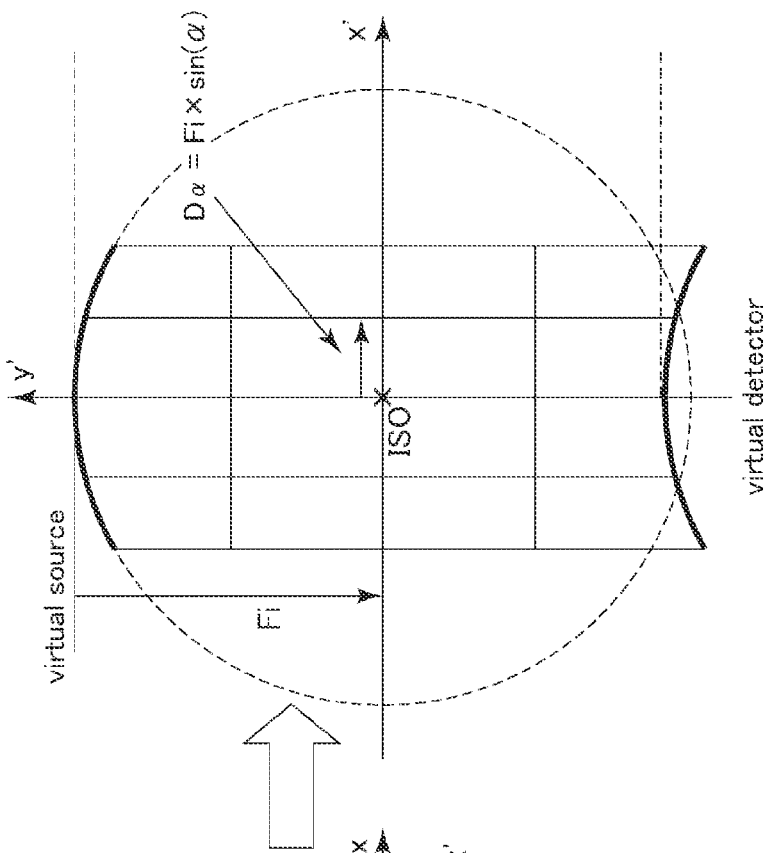
FIGS. 4A and 4B are diagrams showing geometries at fan-para conversion.
Figure 4A:
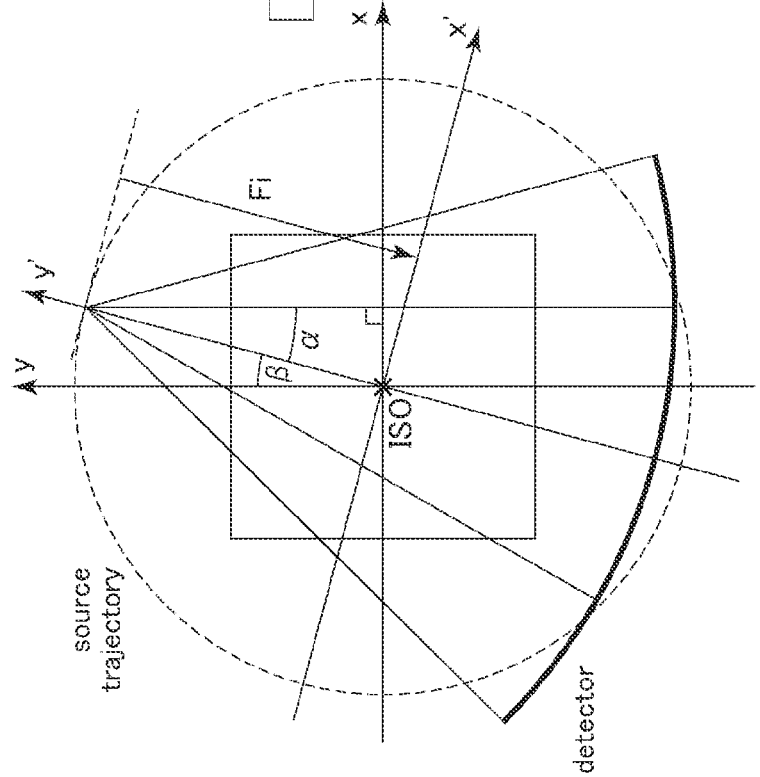

FIGS. 4A and 4B show geometries at fan-para conversion, of which FIG. 4A indicates the geometry of a fan beam and the FIG. 4B indicates the geometry of a parallel beam, respectively.

The fan-para conversion unit 32 performs a rearrangement process and a channel-direction interpolation process on the fan beam projection data of plural views acquired by the data acquisition unit 31 to acquire equally-spaced parallel beam projection data in plural view directions.

The rearrangement process will first be explained. The rearrangement process is a process in which fan beam projection data of plural views are taken apart every data for their rearrangements to thereby acquire parallel beam projection data in which X-ray paths are parallel, with respect to a plurality of view directions.

As is understood from FIGS. 4A and 4B, in the parallel beam projection data acquired after the rearrangement process, the distance $D\alpha$ from the iso-center (the center of rotation of the scan gantry) of an X-ray path corresponding to each data is expressed in $D\alpha = Fi \times \sin(\alpha)$. Here, Fi indicates the distance between an X-ray focal point and the iso-center ISO, and a indicates the rotating angle of each detecting element 24$i$. That is, the parallel beam projection data acquired after the rearrangement process are unequally-spaced parallel beam projection data in which X-ray paths corresponding to respective data are arranged at unequal intervals in the channel direction.

As described above, the scan executed by the data acquisition unit 31 is performed while evenly assigning the predetermined number of views to the rotating angle corresponding to one rotation in such a manner that the rotating angle corresponding to one view becomes substantially equal to the rotating angle $\Delta\alpha$ corresponding to the interval of arrangement of the detecting elements 24$i$ in the channel direction. Therefore, the channel-direction interval between the X-ray paths corresponding to the unequally-spaced parallel beam projection data assumes, in the neighborhood of the iso-center ISO, an interval $\Delta d$ obtained by dividing the interval of arrangement of the detecting elements 24$i$ of the X-ray detector 24 in the channel direction by a projection enlargement rate (also called an X-ray enlargement rate) at the detection surface taken when the iso-center ISO is set as the reference. That is, when a straight line that connects via the neighborhood of the iso-center ISO from an X-ray focal point 21$f$ to the center of one given detecting element 24$i$, and a straight line that connects from the X-ray focal point 21$f$ to a detecting element 24$i$ adjacent to the given detecting element 24$i$ are assumed to exist as shown in FIG. 3, the interval $\Delta d$ becomes equivalent to the distance between the two straight lines in the neighborhood of the iso-center ISO. The spatial resolution of the reconstructed image cannot be rendered higher than the interval $\Delta d$ from a geometric point of view. This interval $\Delta d$ has been considered to be a limit condition that increases the spatial resolution of the reconstructed image to the maximum. Here, the interval $\Delta d$ is assumed to be referred to as a "reference interval". Incidentally, when the interval of arrangement of the detecting elements in the channel direction is about 1 mm, the reference interval $\Delta d$ is about 0.5 mm, for example.

The interpolation process in the channel direction will next be explained. The interpolation process in the channel direction is a process in which an interpolation process is performed on the unequally-spaced parallel beam projection data obtained by the rearrangement process to thereby acquire equally-spaced parallel beam projection data in which X-ray paths corresponding to the respective data are parallel and arranged at equal intervals in the channel direction. Incidentally, upon the interpolation process, the position of each of the X-ray paths at the equally-spaced parallel beam projection data is set in such a manner as to substantially overlap with each of the X-ray paths at the unequally-spaced parallel beam projection data in the neighborhood of the iso-center.

The interpolation process in the channel direction will now be explained while making a comparison between a general method and a method based on the exemplary embodiment.

Figure 5:
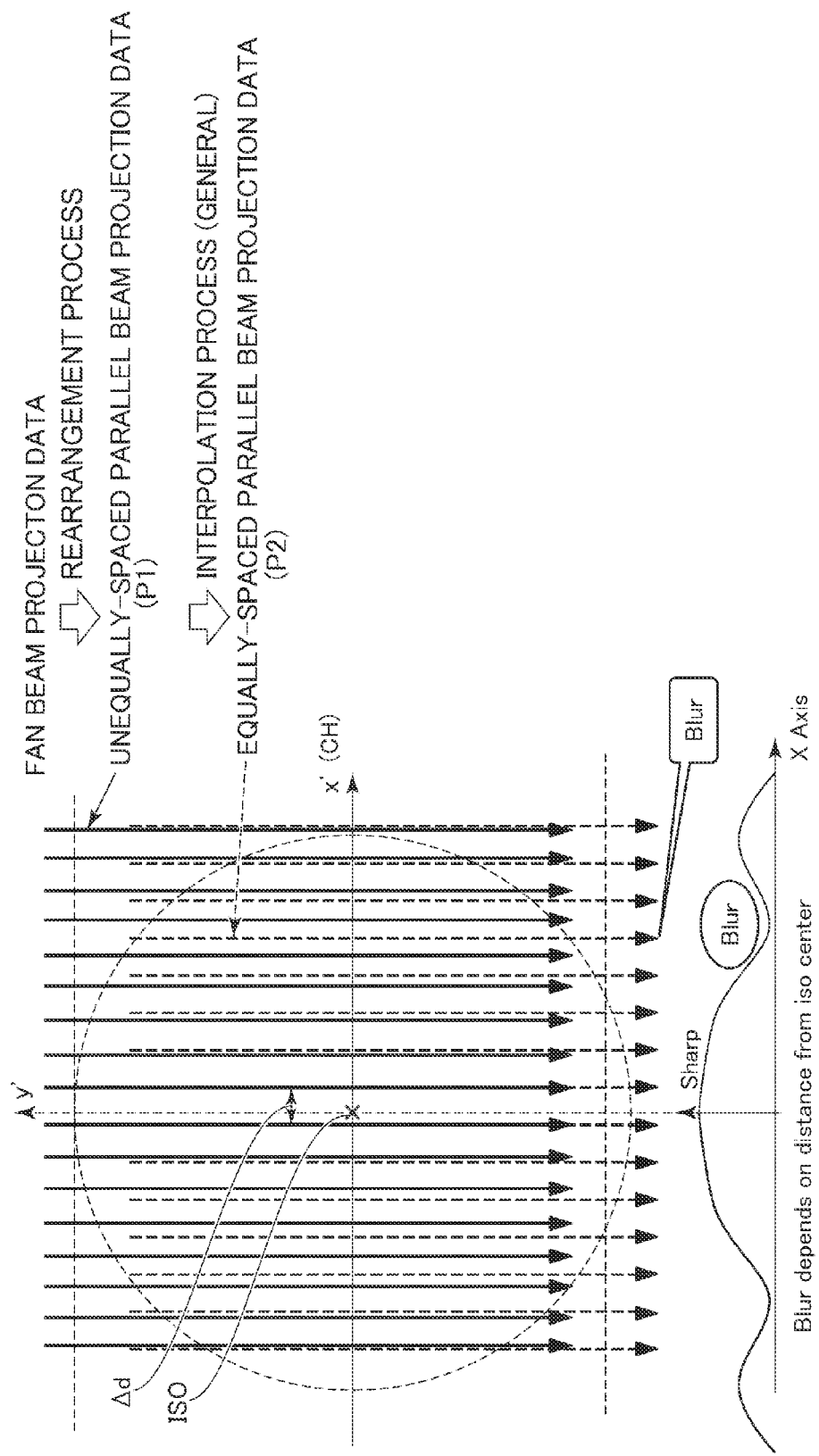
FIG. 5 is a diagram for describing an interpolation process on parallel beam projection data in a channel direction by a conventional method.

FIG. 5 is a diagram for describing the interpolation process in the channel direction by the general method. A group of arrows (non-normalized Fan Data) on the upper side of FIG. 5 is expressed in the form of simplification of X-ray paths at unequally-spaced parallel beam projection data P1. A group of arrows (normalized Fan Data) on the lower side of FIG. 5 is expressed in the form of simplification of X-ray paths at equally-spaced parallel beam projection data P2 after the interpolation process by the general method.

In the general method, as shown in FIG. 5, the interval between the X-ray paths in the channel direction at the equally-spaced parallel beam projection data P2 is set to be substantially equal to the reference interval $\Delta d$. That is, the set of the interval between the X-ray paths at the equally-spaced parallel beam projection data P2 to be acquired, i.e., the sampling interval in the channel direction has already reached such an upper limit that the spatial resolution of the reconstructed image can be rendered highest. Even if sampling is done finer than it, a computational processing amount merely increases and hence such a set as considered not to contribute to an improvement in the spatial resolution is made.

The difference between the interval between the X-ray paths at the unequally-spaced parallel beam projection data P1 and the interval between the X-ray paths at the equally-parallel beam projection data P2 is actually small. A positional relationship between each X-ray path at the unequally-spaced parallel beam projection data P1 and each X-ray path at the equally-spaced parallel beam projection data P2 is however held consistent in the neighborhood of the iso-center ISO, and small displacements begin to take place as the distance from the iso-center ISO increases. With the increase in the distance from the iso-center ISO, the small displacements pile up and gradually increase, thus assuming a local maximum point at a given position. Information necessary to maintain the spatial resolution is lost around the local maximum point. After the local maximum point, the positional displacement of each X-ray path gradually decreases and does not occur in a given position, so that the X-ray paths coincide with each other. Thereafter, the displacement gradually increases and assumes a local maximum point again.

Thus, the spatial resolution, e.g., having a MTF (Modulation Transfer Function) as its index, becomes lower with the periodicity according to the distance from the iso-center ISO.

Figure 6B:
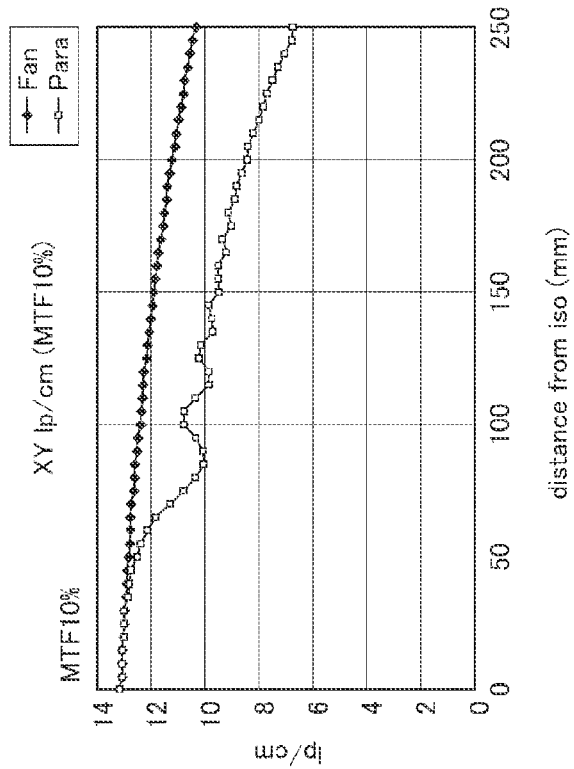
FIGS. 6A and 6B show graphs which illustrate changes in spatial resolution corresponding to the distances from an iso-center at a reconstructed image by a general method and are determined by simulation.
Figure 6A:
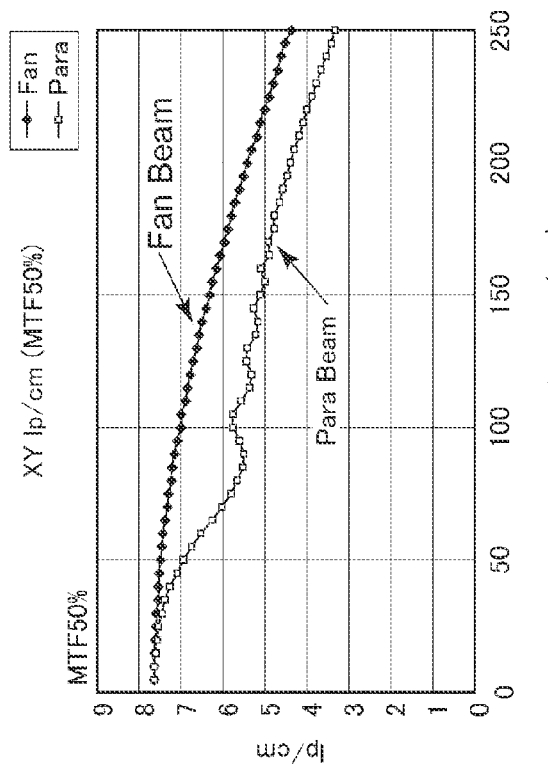

FIGS. 6A and 6B illustrate graphs which show changes in spatial resolution corresponding to the distances from the iso-center ISO in a reconstructed image by a general method and are obtained by simulation. The graph of FIG. 6A is obtained by determining the number of line pairs per cm taken when an MTF value becomes 50%, at respective positions on an image and plotting them. The graph of FIG. 6B is obtained by determining the number of line pairs per cm taken when an MTF value becomes 10%, at respective positions on an image and plotting them. Curves of changes in the spatial resolution of a reconstructed image based on fan beam projection data are placed even at both graphs for reference. Even in these graphs, the manner in which the spatial resolution is reduced with periodicity according to the distance from the iso center ISO is observed at the reconstructed image based on the general method.

In the case of the general method, the amount of positional displacement between the X-ray path at the unequally-spaced parallel beam projection data and the X-ray path at the equally-spaced parallel beam projection data becomes partly large so that the spatial resolution is reduced therearound.

FIG. 7 is a diagram for describing the interpolation process in the channel direction by the method of the exemplary embodiment. A group of arrows on the upper side of FIG. 7 is represented in the simplified form of X-ray paths at unequally-spaced parallel beam projection data P1. A group of arrows on the lower side of FIG. 7 is represented in simplified form of X-ray paths at equally-spaced parallel beam projection data P3 after the interpolation process by the method of the exemplary embodiment.

In the method of the exemplary embodiment, as shown in FIG. 7, the interval between the X-ray paths at the equally-spaced parallel beam projection data P3 in the channel direction is set smaller than a reference interval Δd. Further, the interval therebetween is set to be substantially the same as 1/N (where N: integer greater than or equal to 2) of the reference interval Δd.

Seemingly, even if done in this manner, this might not seem like a contribution to an improvement in the spatial resolution. In fact, however, when the interval between the X-ray paths at the equally-spaced parallel beam projection data P3 in the channel direction is set smaller than the reference interval Δd in this way, the opportunity that pre-interpolation data high in accuracy (i.e., each data itself at the unequally-spaced parallel beam projection data P1 or post-interpolation data close thereto) is used in a back-projection process can be increased, so that a reduction in the spatial resolution of the reconstructed image can be suppressed.

Further, when the interval between the X-ray paths at the equally-spaced parallel beam projection data P3 in the channel direction is set to 1/N (where N is an integer greater than or equal to 2) of the reference interval Δd, data themselves at the unequally-spaced parallel beam projection data P1 or post-interpolation data close thereto can be more included in the equally-spaced parallel beam projection data P3, thus making it possible to more suppress a reduction in the spatial resolution of the reconstructed image.

Incidentally, the larger the integer N, the more the effect of suppressing the reduction in the spatial resolution increases. The effect however gradually maxes out, whereas the amount of computational processing continues to increase. Therefore, when the balance between the effect and the amount of calculation is taken into consideration, for example, N may be set in a range from about 2 to 4.

The above interpolation process, may be used, for example, in addition to linear interpolation (primary interpolation), multidimensional interpolation such as spline interpolation, Lagrange interpolation, Newton interpolation, bi-linear interpolation, etc.

When multidimensional interpolation is used as the interpolation process, the order of the interpolation process may be changed according to the distance of each X-ray path corresponding to data attempted to be acquired by this interpolation process from the iso-center ISO. For example, when the distance decreases, the order of the interpolation process may be set to decrease. As the distance increases, the order of the interpolation process may be set to increase. If done in this manner, an interpolation process more appropriate to high and low tendencies of the spatial resolution as seen in the radial direction from the center corresponding to the iso-center ISO in the reconstructed image can be applied, and hence a reduction in the spatial resolution can be expected to be further suppressed.

Assigning weights to the original data used in the interpolation process may be changed according to the distance between each X-ray path corresponding to data attempted to be obtained by this interpolation process and the X-ray path corresponding to the original data used in this interpolation process. That is, nonlinearity may be applied to the weighting. For example, when the distance decreases, the weight may be made large, whereas as the distance increases, the weight may be made small. If done in this manner, when the X-ray path corresponding to the post-interpolation data can be determined to be enough close to the X-ray path corresponding to the original data used in the interpolation process, the weight to be assigned to the original data can be made larger as compared with the linear interpolation, whereby data closer to actual data can be obtained and a reduction in the spatial resolution can be expected to be further suppressed.

Incidentally, the rearrangement process and the interpolation process in the channel direction may respectively be performed on the algorithm stepwise in parts or may be performed collectively in the form of single processing.

The back-projection processing unit 33 performs a back-projection process on the equally-spaced parallel beam projection data in the plural view directions acquired by the fan-para conversion unit 32 to reconstruct an image. As the back-projection process, there can be used, for example, a filtered back-projection process, a convolution back-projection process, etc. The filtered back-projection process is of a process which multiplies Fourier transformation of projection data by a reconstruction function (filter function) in a frequency space and performing inverse Fourier transformation to reconstruct an image. The convolution back-projection process is of a process which determines inverse Fourier transformation of a reconstruction function and overlays it on projection data on a real space, i.e., performs convolution on it, followed by being back-projected, thereby reconstructing an image.

The flow of an image generating process in the X-ray CT apparatus according to the exemplary embodiment will be explained.

Figure 8:
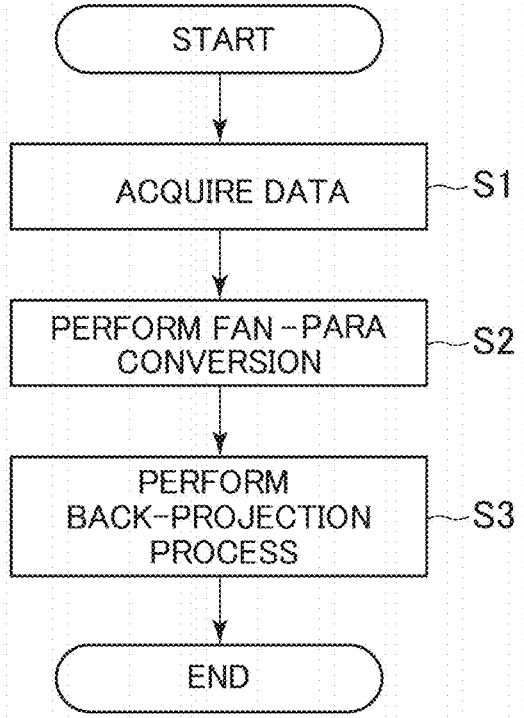
FIG. 8 is a flow chart illustrating the flow of an exemplary image generating process.

FIG. 8 is a flow chart showing the flow of the image generating process in the X-ray CT apparatus according to the exemplary embodiment.

At Step S1, the data acquisition unit 31 runs a scan to acquire fan beam projection data of plural views. At this time, for example, a scan is done while assigning views for acquiring actual data to a rotating angle corresponding to one rotation of scan for every rotating angle corresponding to the interval of arrangement of detecting elements 24i. Incidentally, when fan beam projection data of view numbers corresponding to it are generated inclusive of interpolation in each view direction by the actual data, views for performing acquisition of the actual data are assigned at least 1200 or more to the rotating angle corresponding to one rotation of scan.

At Step S2, the fan-para conversion unit 32 performs a rearrangement process and an interpolation process in a channel direction on the fan beam projection data of the plural views acquired at Step S1 to thereby perform fan-para conversion, thereby acquiring equally-spaced parallel beam projection data. At this time, the interval between X-ray paths in the channel direction is set to an interval equivalent to 1/N (where N is an integer ranging from 2 to 4, for example) of the reference interval Δd.

At Step S3, the back-projection process is performed on the equally-spaced parallel beam projection data acquired at Step S2 to reconstruct an image.

A description will now be made of a result of comparison between a reconstructed image by a generally-used method (hereinafter called "general method") and a reconstructed image by a method (hereinafter called "exemplary method") based on the exemplary embodiment.

Figure 9:
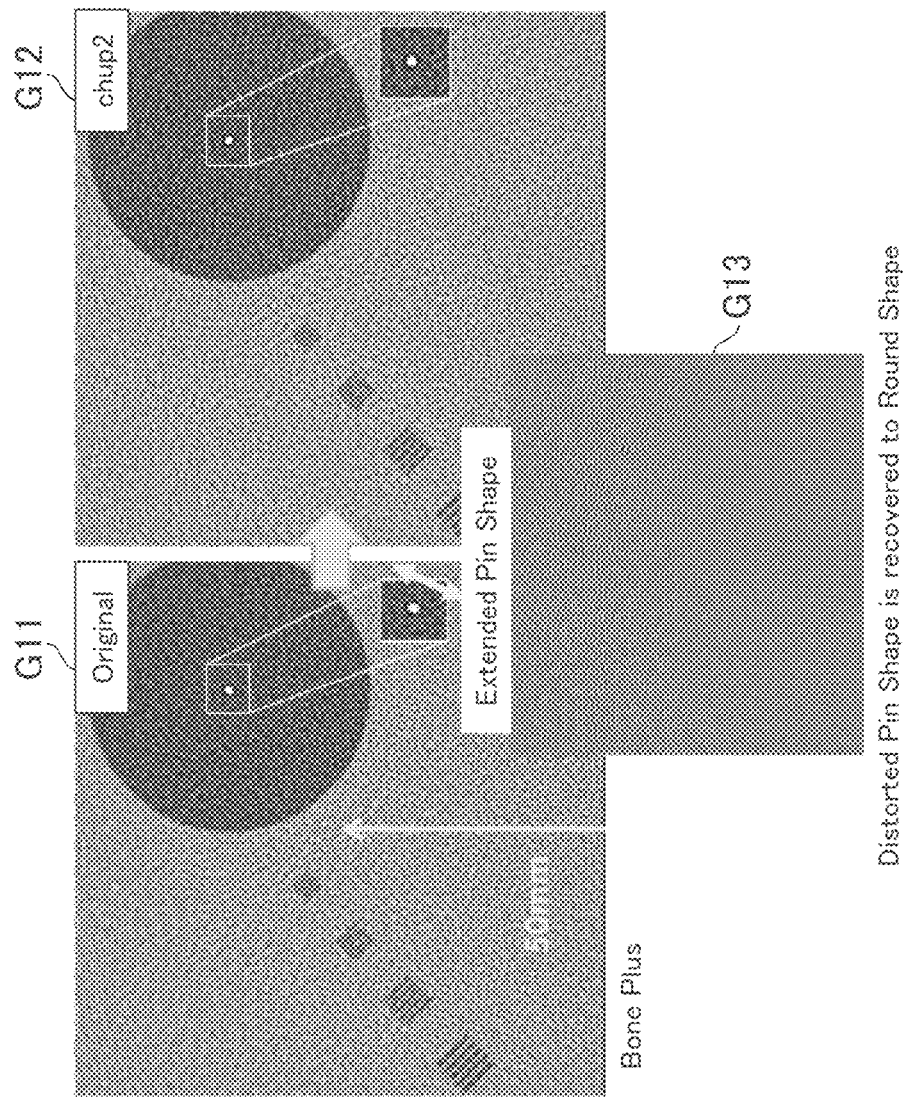
FIG. 9 is a diagram showing a first example of comparison between an image based on a general method and an image based on the exemplary method.

FIG. 9 is a diagram showing a first example of comparison between an image by the general method and an image by the exemplary method. The first example is an example in which a phantom for MTF measurement is placed so as to assume a position where its center is spaced a radius 50 mm from an iso-center ISO and is scanned. An image G11 (Original) on the left side is an original image based on the general method and acquired when the interval between X-ray paths at the interpolation process as seen in the channel direction is set to the reference interval Δd. An image G12 (chup2) on the right side is an image based on the present method and obtained when the interval between X-ray paths at the interpolation process as seen in the channel direction is set to ½ of the reference interval Δd, i.e., sampling in the channel direction is set to be as double as dense. An image G13 on the lower center side is an image corresponding to a difference between these. As shown in FIG. 9, in the original image G11 based on the general method, a pin in the phantom for the MTF measurement extends in the channel direction (the radial direction centering on the iso-center). On the other hand, it is understood that in the image G12 based on the exemplary method, its pin is represented as the original circular shape and has been improved.

Figure 10:
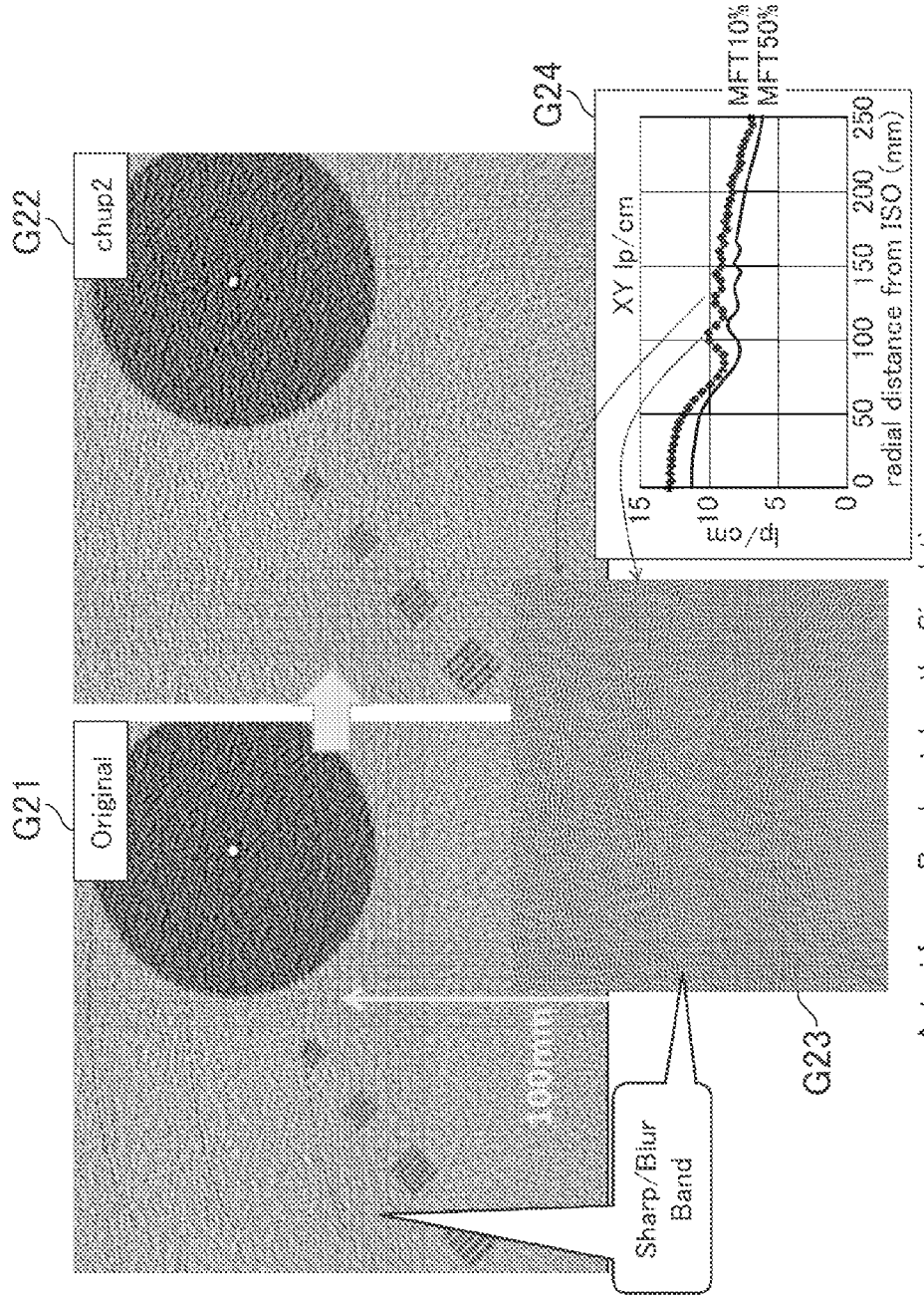
FIG. 10 is a diagram showing a second example of comparison between an image based on the general method and an image based on the exemplary method.

FIG. 10 is a diagram showing a second example of comparison between an image based on the general method and an image based on the exemplary method. The second example is an example in which the same MTF measurement phantom as that shown in the first comparative example is placed so as to assume or take a position where its center is spaced a radius 100 mm from an iso-center ISO and is scanned. An image G21 (Original) on the left side is an original image (interval between X-ray paths="reference interval") based on the general method. An image G22 (chup2) on the right side is an image (interval between X-ray paths=½ of "reference interval") based on the exemplary method. An image G23 on the lower center side is an image corresponding to a difference between these. A graph 24 lateral to the image G23 is obtained by plotting line pairs per cm (lp/cm) at the time that the MTF value becomes 10%, and line pairs per cm (lp/cm) at that time that the MTF value becomes 50%, with respect to the distance from the iso-center ISO. In the original image G21 based on the general method, as is understood even from the differential image shown in FIG. 10, a Sharp/Blur band has occurred over the circumferential direction according to the distance from the iso-center ISO. On the other hand, the image G22 based on the exemplary method is improved to be an image in which the occurrence of such a band is suppressed and its spatial resolution is flat.

Figure 11:
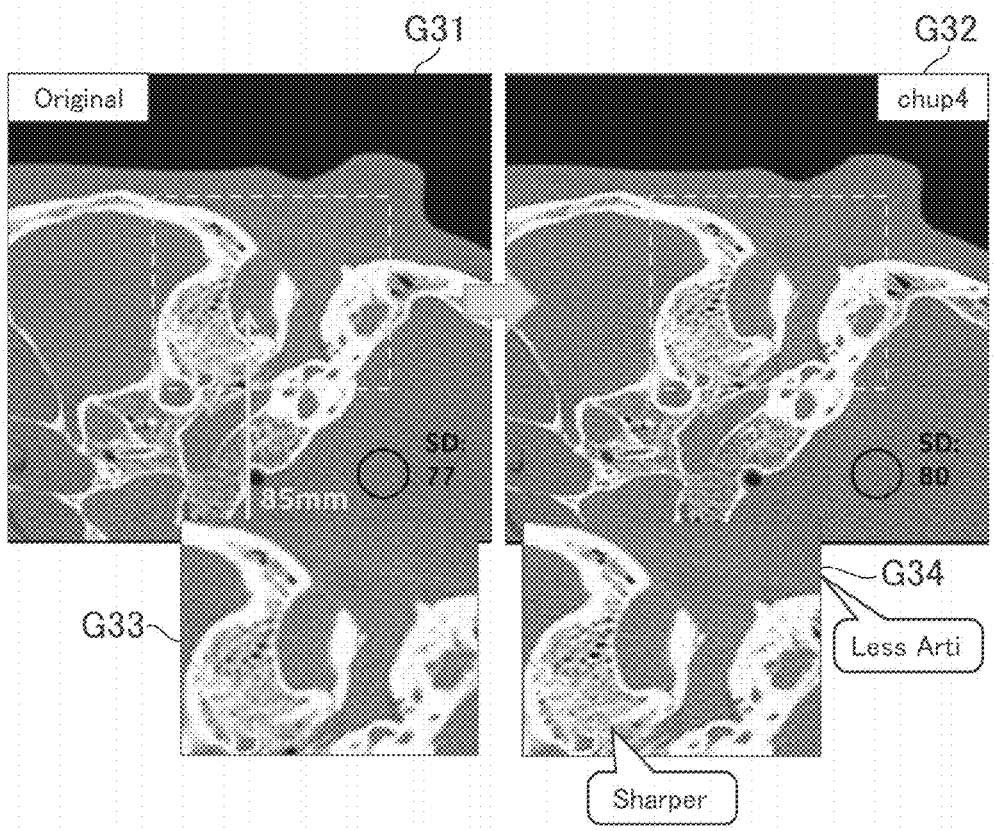
FIG. 11 is a diagram showing a third example of comparison between an image based on the general method and an image based on the exemplary method.

FIG. 11 is a diagram showing a third example of comparison between an image based on the general method and an image based on the exemplary method. The third example is an example in which a head phantom is scanned. Its image indicates the structure of a bone region of the inner ear lying in a position spaced a radius 85 mm from an iso-center. An image G31 on the upper left side is an original image based on the general method and obtained when the interval between each X-ray path at the interpolation process in the channel direction is set to the reference interval Δd. An image G32 (chup4) on the upper right side is an image based on the exemplary method and obtained when the interval between each X-ray path at the interpolation process in the channel direction is set to ¼ of the "reference interval", i.e., sampling in the channel direction is set to be four times as dense. An image G33 on the lower left side is an enlarged view of a region surrounded by a broken line in the image G31. An image G34 (ch2v2) on the lower right side is an enlarged view of a region surrounded by a broken line in the image on the upper right side. It is understood that even at a region away from the iso-center ISO, its spatial resolution has been improved in the image based on the exemplary method.

Figure 12:
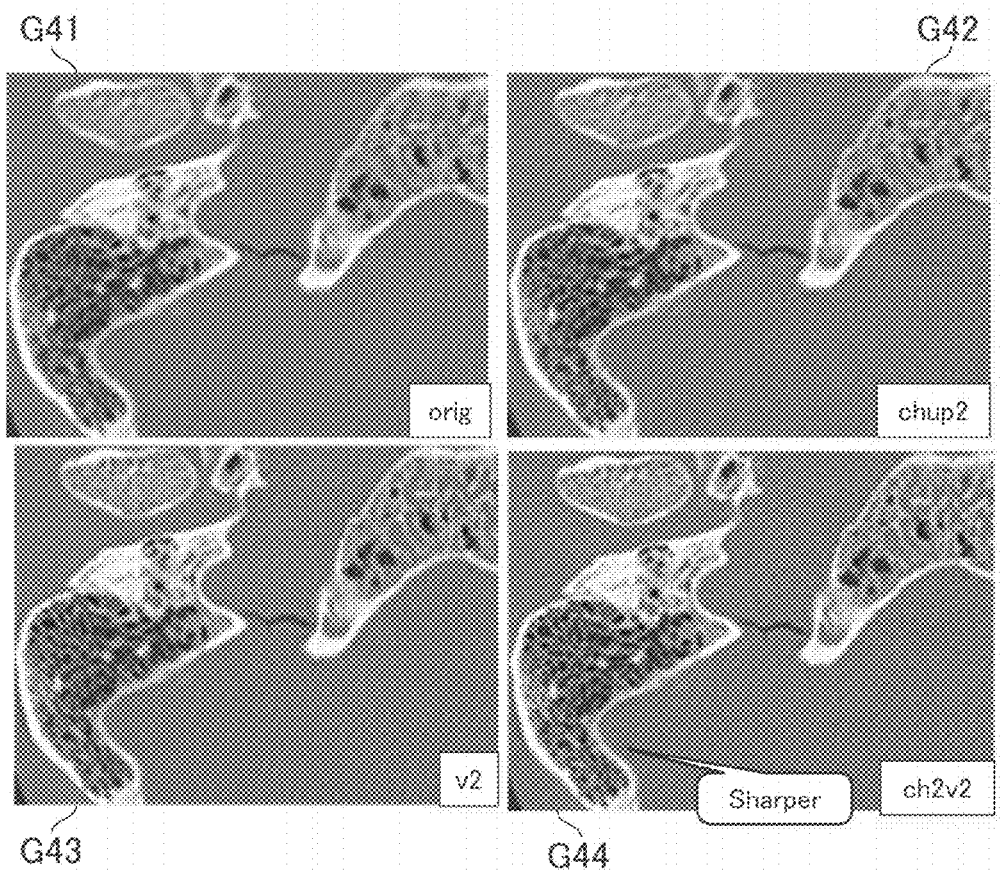
FIG. 12 is a diagram showing a fourth example of comparison between an image based on the general method and an image based on the exemplary method.

FIG. 12 is a diagram showing a fourth example of comparison between an image based on the general method and an image based on the exemplary method. The fourth example is an example in which a head phantom is scanned. Its image indicates the structure of a local region of the bone of the inner ear. An image G41 (Original) on the upper left side is an original image based on the general method and obtained when the interval between each X-ray path at the interpolation process in the channel direction is set to the reference interval Δd. An image G42 (chup2) on the upper right side is an image based on the exemplary method and obtained when the interval between each X-ray path at the interpolation process in the channel direction is set to ½ of the reference interval Δd, i.e., sampling in the channel direction is set to be twice as dense. An image G43 (v2) on the lower left side is one obtained when the number of views for performing the acquisition of actual data is set to twice (1600 or more per rotation) the normal number, i.e., sampling in the view direction is set to be twice as dense. An image G44 (ch2v2) on the lower right side is one obtained when sampling in both of the channel and view directions are set to be twice as dense as normal. As is understood from FIG. 12, the image obtained when the sampling in both channel and view directions are set to be twice as dense as normal is highest in spatial resolution.

Thus, according to the exemplary embodiment, the equally-spaced parallel beam projection data are acquired in such a manner that when the fan-para conversion is performed, the interval between each radiation path in the channel direction becomes the interval smaller than the reference interval obtained by dividing the interval of arrangement of the detecting elements in the channel direction by the projection enlargement rate at the detection surface of the detector taken when the so-called iso-center is set as the reference. Therefore, the pre-interpolation data (i.e., data before the interpolation processing) high in accuracy or the post-interpolation data (i.e., data after the interpolation processing) close thereto can be more used in the back-projection process. Even if the fan-para conversion is performed, a reduction in the spatial resolution of the reconstructed image can be suppressed.

Incidentally, various changes and additions and the like can be made to the exemplary embodiment without departing from the scope or spirit of the disclosure.

For example, although the exemplary embodiment is implemented using an X-ray CT apparatus, an image generating apparatus that performs the above image generating process is also one example illustrative of an embodiment of the invention. A program for allowing a computer to function as such an image generating apparatus, a storage medium in which the program has been stored, or the like is also one example illustrative of an embodiment of the invention.

For example as well, although the exemplary embodiment is implemented using an X-ray CT apparatus, the disclosure is applicable even to a PET-CT apparatus or SPECT-CT apparatus in which the X-ray CT apparatus and PET or SPECT are combined together, a general imaging apparatus, etc.

What is claimed is:

1. A radiation tomographic imaging apparatus comprising:
a radiation source;
a detector having a plurality of detecting elements arranged in a channel direction;
an acquirer configured to acquire fan beam projection data of a plurality of views by a scan for rotating the radiation source and the detector about a target;
a converter configured to perform a rearrangement process and an interpolation process on the acquired fan beam projection data to generate equally-spaced parallel beam projection data in which channel direction intervals are equal there between, the interpolation process performed with respect to a plurality of view directions;
a reconstructer configured to perform a back-projection process on the equally-spaced parallel beam projection data to thereby reconstruct an image;
wherein the channel direction intervals between the equally-spaced parallel beam projection data are smaller than a reference interval obtained by dividing an interval between the detecting elements in the channel direction by a projection enlargement rate at a detection surface of the detector when a center of rotation of each of the radiation source and the detector is set as a reference;
wherein, near the center of rotation, positions of radiation paths of the equally-spaced parallel beam projection data in the channel direction overlap with positions of radiation paths of unequally-spaced parallel beam projection data lying next to each other in the channel direction;
wherein the unequally-spaced parallel beam projection data is generated by the rearrangement process on the fan beam projection data for a plurality of views; and
wherein the interval between the equally-spaced parallel beam projection data in the channel direction is 1/N, where N of the reference interval is any integer ranging 2 to 4.

2. The radiation tomographic imaging apparatus according to claim 1, wherein the converter is configured to change an order of the interpolation process according to a distance of data attempted to be generated by the interpolation process from the center of rotation.

3. The radiation tomographic imaging apparatus according to claim 2, wherein the converter is configured to change a weighting of original data used in the interpolation process according to a distance between a position of data attempted to be generated by the interpolation process and a position of the original data.

4. The radiation tomographic imaging apparatus according to claim 1, wherein the converter is configured to change a weighting of original data used in the interpolation process according to a distance between a position of data attempted to be generated by the interpolation process and a position of the original data.

5. The radiation tomographic imaging apparatus according to claim 1, wherein the acquirer is configured to assign views for performing the acquisition of actual data to a rotating angle per rotation of each of the radiation source and the detector 1200 more to thereby acquire the fan beam projection data of the plural views.

* * * * *